United States Patent
Poellmann (12)

(10) Patent No.: US 6,458,596 B1
(45) Date of Patent: Oct. 1, 2002

(54) METHOD FOR SENSING THE FAULTY POSITIONING OF AN OPTICALLY EVALUATABLE TEST STRIP AND A TEST STRIP THEREFOR

(75) Inventor: Norbert Poellmann, Eching (DE)

(73) Assignee: LRE Technology Partner GmbH, Munich (DE)

( * ) Notice: Subject to any disclaimer, the term of this patent is extended or adjusted under 35 U.S.C. 154(b) by 0 days.

(21) Appl. No.: 09/614,431

(22) Filed: Jul. 12, 2000

(30) Foreign Application Priority Data

Jul. 14, 1999 (DE) .......................... 199 32 846

(51) Int. Cl.⁷ .......................... G01N 21/77; C12M 1/34; C12Q 1/54
(52) U.S. Cl. .................. 436/169; 435/287.7; 435/14; 435/4
(58) Field of Search ............... 435/14, 4, 25, 435/287.7; 422/50, 68.1; 436/169

(56) References Cited

U.S. PATENT DOCUMENTS 5,945,341 A * 8/1999 Howard, III

OTHER PUBLICATIONS

WO 9607907A1. Patel (1996). Optically readable strip for analyte detection having on–strip orientation index.*

Derwent Acc No. 1998–090886 of JP 09318544A (1997). Test substance paper analyser for urine analysis using optical radiation technique.*

* cited by examiner

Primary Examiner—Ralph Gitomer
Assistant Examiner—Mahreen Chaudhry
(74) Attorney, Agent, or Firm—McCormick, Paulding & Huber LLP

(57) ABSTRACT

In a method for recognizing the faulty positioning of an optically evaluatable test strip in a device for measuring a substance in a liquid, especially for blood sugar determination, the fluid to be investigated is applied to a test field (24) of a test strip (20) and the change in the reflection or transmission ability of the test field (24) thereby effected is captured and evaluated. A measuring field (16) of the measuring device associated with the test field of the test strip is divided into at least two measuring areas which, with respect to the insertion direction of the test strip, are arranged behind one another and are separately sensed. The test strip (20) has at least in the area lying in front of the test field (24), with respect to the insertion direction zones (28, 29) arranged behind one another and of different reflection or transmission abilities. The difference between the measured values of the two measured areas is formed and compared with a pre-given threshold value, and upon an exceeding of the threshold value a signal indicating faulty test strip positioning is created.

1 Claim, 1 Drawing Sheet

METHOD FOR SENSING THE FAULTY POSITIONING OF AN OPTICALLY EVALUATABLE TEST STRIP AND A TEST STRIP THEREFOR

FIELD OF THE INVENTION

The invention concerns a method for sensing the faulty positioning of an optically evaluatable test strip in a measuring device for measuring a substance in a fluid, especially for blood sugar determination, wherein the fluid to be investigated is applied to the test field of a test strip and the change in the reflection or transmission ability of the test field caused thereby is captured and evaluated.

BACKGROUND OF THE INVENTION

In a blood sugar measurement carried out by a patient itself the patient applies a drop of blood onto the test field of a test strip which test field is then optically measured. Thereby, a detector for example captures the color change of the test field, which is caused by the dropping of the blood onto the test field. A correct value is then obtained only if previously a correct empty value measurement has been carried out on the unused test field. If, for example, the test strip is not correctly inserted into the measuring device, the measuring optic system then does not sense the unused test field but instead senses the carrier foil of the test strip which differs from the test field by having a different optical reflection or transmission characteristic. In this case the empty measurement is a mistaken one which necessarily leads to incorrect measurement results.

A method is known from WO 96 07 907 for detecting the faulty positioning of an optically evaluatable test strip in order to enable one to determine whether the test strip is correctly inserted into the measuring device, that is without the test strip being oriented upside down. In this case the test strip in the area between its input end and the test field has a so called orientation indication, whose reflection ability differs from the reflection ability of the remaining portion of the upper surface of the test strip carrier material. Upon insertion of the test strip this orientation indicator zone, for example a black bar on a white carrier material, is captured by the measuring optic system, as a result of which the device presumes that the test strip has been correctly inserted into the measuring device. If the measuring optic system on the other hand does not sense this orientation indicator zone the measuring device presumes that the strip has been incorrectly inserted into the device. The patient is informed of this by an indication on the indicator mechanism of the measuring device to check and change the position of the measuring strip. This device cannot however determine whether the test strip has been correctly so fully inserted into the measuring device that the measuring field can in its entirety be captured by the measuring optic system.

The invention has as its object the provision of a method which avoids the above mentioned difficulty and allows a determination to be made of whether the test strip is correctly positioned relative to the measuring optic systems so that only the test field, and not in a faulty way, a portion of the upper surface of the carrier of the test strip is captured by the measuring optic system.

SUMMARY OF THE INVENTION

The above mentioned object is solved by a method of the above-mentioned kind wherein the measuring field for measuring the test field of the test strip is divided into at least two measuring areas with the different measuring areas being arranged behind one another in the insertion direction of the test strip and with the separate measuring areas being separately sensed, and wherein the test strip has zones of different reflection or transmission abilities which zones lie behind one another and in front of the test field in respect to the insertion direction of the test strip, and wherein the difference between the measured values obtained for the two measuring areas is formed and compared with a pregiven threshold value, and a faulty positioning indicating signal being produced when the difference between the measured values exceeds the threshold value.

If the test strip is correctly positioned in the measuring device both measuring areas of the device lie within the test field. The measuring optic systems associated with the measuring areas capture only areas of the test field which in normal cases, in the empty value measurement as well as in the actual measurement, deliver at least nearly equal reflection or transmission values. On the other hand, if the test strip is not correctly positioned relative to the measuring optic systems, for example not inserted deeply enough into the device, the two measuring areas fall either onto zones of different reflection or transmission values or one of the measuring areas falls into the measuring field while the other measuring area comes into registration with one of the mentioned zones. In any event, the two measuring optic systems associated with the measuring areas in this case deliver such different values that the mentioned threshold value is exceeded, and accordingly a corresponding indication is produced by means of which the user is, for example, instructed to check the position of the test strip in the measuring device and, if needed, to correct the position.

The invention further concerns a test strip, for carrying out the above described method, with a carrier and a test field for receiving the investigated liquid, with the carrier in accordance with the invention at least in the area which, with reference to the test strip insertion direction, lies in front of the test field having zones of different reflection or transmission abilities, the dimensions of which zones in the insertion direction at least nearly correspond to the measurements of the measuring areas. Preferably, the zones of different reflection or transmission abilities are formed by strips of different color, which for example can be printed onto the carrier material of the test strip.

As the measuring apparatus, a measuring device can be used such as that described in German Utility Model Registration No. 2 962 037 2 of the applicant with the restriction that the measuring optic systems associated with the two measuring areas be arranged behind one another in the test strip insertion direction.

The following description explains the invention in connection with the accompanying drawing by way of an exemplary embodiment.

BRIEF DESCRIPTION OF THE DRAWINGS

The single figure, FIG. 1, of the drawing shows a schematic plan view of a portion of a strip support surface of a measuring device and of a test strip lying on that surface.

DETAILED DESCRIPTION OF PREFERRED EMBODIMENT

Figure 1:
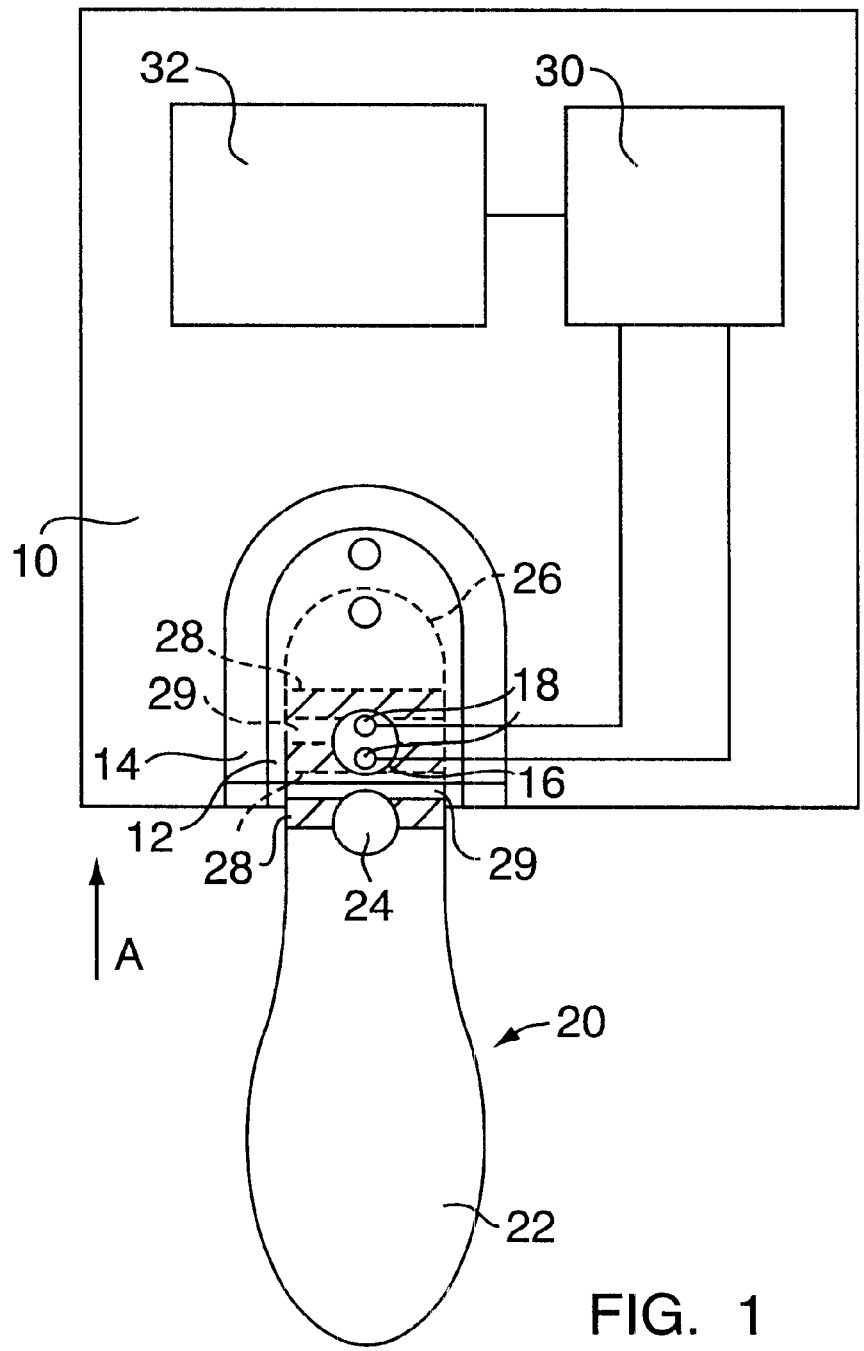

In FIG. 1, one sees a schematic representation of the input section 10 of an otherwise non-illustrated measuring device for the optical measurement of test strips, with the input section 10 having a test strip support surface 12. The device can basically be formed, for example, as described in German Ufility Model Registration No. 2 96 203 72. It has accordingly a measuring aperture 14 arranged above the test strip support surface 12 and having a measuring field 16 inside of which are two measuring optics 18 arranged behind one another in respect to the insertion direction, indicated by the arrow (A), of a test strip indicated generally at 20. Each measuring optic 18 is thereby arranged in one half of the circular shaped measuring field 16.

The test strip 20 includes a carrier made of a predominantly hydrophobic material with a grip section 22, a test field 24 and an input end 26 at the end opposite to the grip section 22. The test field 24 consists of a hydrophilic material, which contains a test reagent selected to create a reaction for the looked for substance in the liquid dropped onto the test field.

In the area lying between the input end 26 and the test field 24 colored transverse bars 28 are printed onto the upper surface of the test strip carrier material, which bars 28 are separated from one another by unprinted sections 29 of the carrier upper surface. The width and the spacing of the strips 28, 29 in the insertion direction correspond at least nearly to the range of the two measuring areas inside of the measuring field 16. As a result of this, upon the insertion of the test strip in the direction of the arrow (A) into the measuring device the two measuring optics 18 at least in the area directly preceding the test field 24 lie over differently colored zones, until the test strip 20 has been so far inserted into the measuring device that the test field 24 lies under the measuring field 16 of the measuring aperture 14 and thereby both measuring optics 18 lie above the test field 24.

The two measuring optics 18 are connected with a measuring and evaluation circuit 30 in which the difference between the values measured by the two measuring optics 18 is formed. This difference value is then compared with a pre-given threshold value. If the threshold value is exceeded the evaluation circuit 30 creates an output signal which actuates an indicator device 32 to produce a suitable indication by means of which the user is directed to check the position of the test strip 20 in the measuring device. If the difference value is below the threshold value it can be assumed that the test strip is correctly positioned and that the measuring field 16 registers with the test field 24.

What is claimed is:

1. A method for recognizing the faulty positioning of an optically evaluatable test strip in a measuring device for measuring a substance in a liquid, wherein the fluid to be investigated is applied to a test field (24) of a test strip (20) and the change in the optical reflection or transmission ability of the test field which is thereby effected is captured and evaluated, characterized in that a measuring field (16) associated with the test field of the test strip (20) in the measuring device is divided into at least two measuring areas, which measuring areas are arranged one behind the other in relation to the insertion direction of the test strip into the measuring device and separately sense two corresponding measured areas of a test strip inserted into the measuring device and which two measured areas of the test strip are arranged in relation to the insertion direction of the test strip similarly to the arrangement of the measuring areas in relation to the insertion direction of the test strip to obtain measured values of the reflection or transmission abilities of the two measured areas of the test strip, the test strip (20) at least in an area lying in front of the test field (24) in the insertion direction has zones (28, 29) of different reflection or transmission abilities lying in succession and adjacent to one another in respect to the insertion direction, and that the difference between the measured values of the reflection or transmission ability obtained for the two measured test strip areas is formed and compared with a pre-given threshold value, whereupon if the test strip is correctly positioned in the measuring device the two measured areas of the test strip are both located in the test field and deliver nearly equal measured values and if the test strip is faultily positioned at least one measured area falls outside of the test field onto a zone of different reflection or transmission ability so that different measured values are delivered and the threshold value is exceeded to create a faulty positioning indicating signal.

* * * * *